US009928985B2

(12) United States Patent
Lemaitre

(10) Patent No.: US 9,928,985 B2
(45) Date of Patent: Mar. 27, 2018

(54) ROBUST EMITTER FOR MINIMIZING DAMAGE FROM ION BOMBARDMENT

(71) Applicant: General Electric Company, Schenectady, NY (US)

(72) Inventor: Sergio Lemaitre, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 89 days.

(21) Appl. No.: 15/056,431

(22) Filed: Feb. 29, 2016

(65) Prior Publication Data

US 2017/0250050 A1 Aug. 31, 2017

(51) Int. Cl.
*H01J 35/06* (2006.01)
*A61B 6/00* (2006.01)

(52) U.S. Cl.
CPC ................ *H01J 35/06* (2013.01); *A61B 6/40* (2013.01); *A61B 6/461* (2013.01); *A61B 6/54* (2013.01); *H01J 2235/06* (2013.01)

(58) Field of Classification Search
CPC ......... H01J 35/06; H01J 2235/06; A61B 6/40; A61B 6/461; A61B 6/54
USPC ................................................. 378/121, 136
See application file for complete search history.

(56) References Cited

U.S. PATENT DOCUMENTS

| | | | | |
|---|---|---|---|---|
| 8,401,151 | B2 | 3/2013 | Frontera et al. | |
| 8,831,178 | B2 | 9/2014 | Lemaitre | |
| 2014/0079187 | A1 * | 3/2014 | Zhang ..................... | H01J 35/06 378/136 |

* cited by examiner

*Primary Examiner* — Courtney Thomas
(74) *Attorney, Agent, or Firm* — Boyle Fredrickson, S.C.

(57) ABSTRACT

In the present invention, an X-ray tube is provided including a cathode assembly with a cathode cup, and an emitter disposed within the cup configured to emit an electron beam therefrom. The emitter is formed with a central portion including legs with varying lengths and/or spaces formed therein. The legs including spaces of varying lengths provides additional emissive material at the center of the emitter to better withstand strikes from ions formed within the X-ray tube. The legs of varying overall lengths provides a void in the emitter through which the ions can pass without striking the emitter.

18 Claims, 5 Drawing Sheets

ROBUST EMITTER FOR MINIMIZING DAMAGE FROM ION BOMBARDMENT

BACKGROUND OF INVENTION

The subject matter disclosed herein relates to X-ray tubes, and in particular to emitters for use in X-ray tubes.

Presently available medical X-ray tubes typically include a cathode assembly having an emitter and a cup. The cathode assembly is oriented to face an X-ray tube anode, or target, which is typically a planar metal or composite structure. The space within the X-ray tube between the cathode and anode is evacuated.

X-ray tubes typically include an electron source, such as a cathode, that releases electrons at high acceleration. Some of the released electrons may impact a target anode. The collision of the electrons with the target anode produces X-rays, which may be used in a variety of medical devices such as computed tomography (CT) imaging systems, X-ray scanners, and so forth.

To improve the useful life of the emitters used to generate the electron beams and thus the useful life of the X-ray tubes, a flat surface emitter (or a 'flat emitter') may be positioned within the cathode cup with the flat surface positioned orthogonal to the anode, such as that disclosed in U.S. Pat. No. 8,831,178, incorporated herein by reference in its entirety. In the '178 patent a flat emitter with a rectangular emission area is firmed with a very thin material having electrodes attached thereto, which can be significantly less costly to manufacture compared to conventionally wound (cylindrical or non-cylindrical) filaments and may have a relaxed placement tolerance when compared to a conventionally wound filament.

X-ray tubes having cathodes with flat emitters can control the flow of electrons from the emitter to the target using a grid electrode. The electron emission originating from the surface of a thermoionic electron emitter, the flat emitter, strongly depends on the "pulling" electric field generated by the X-ray tube's anode. For enabling fast on/off switching of the tube, it is known from the relevant prior art that X-ray tubes of the rotary-anode type may be equipped with a grid electrode placed in front of the electron emitter. To shut off the electron beam completely, a bias voltage is applied to the grid electrode which generates a repelling field and is usually given by the absolute value of the potential difference between the electron emitter and the grid electrode. The resulting electric field at the emitter surface is the sum of the grid and the anode generated field. If the total field is repelling on all locations on the electron emitter, electron emission is completely cut off.

Additionally, in X-ray tubes employing a flat filament/emitter and focal spot control via electrostatic focusing, such as disclosed in co-owned U.S. Pat. No. 8,401,151, entitled "X-Ray Tube For Microsecond X-Ray Intensity Switching" the entirety of which is expressly incorporated by reference herein for all purposes, the electron beam drifts a distance of several centimeters past the anode in electric field free region before reaching the target. Due to the increased travel distance more residual gas ions are produced.

However, in all X-ray tubes an amount of residual gas is present within the tube as a result of the manufacturing processes for the tubes. When electrons generated by the emitters and drawn towards the anode strike the residual gas, the gas becomes ionized. As this ion charge is opposite that of the electrons generated by the emitter and ions are much heavier than electrons, the ions are drawn to the center 300 of the emitter 1000 where these ions strike the emitter 1000 causing damage to the emitter surface through sputtering and/or local heating as shown in FIG. 3. Over time, this damage accumulates and can completely break or sever the ribbon of material forming the emitter 1000, thereby severing the circuit for current flow through the emitter and rendering the X-ray tube inoperative.

To limit the ion bombardment of prior art emitters, various types of ion barriers are utilized. These ion barriers are disposed upstream from the emitter and operate to draw the ions in or onto the barriers or inhibit ions to travel past the barriers. However, while effective in preventing ions from bombarding the emitters, these ion barriers create significant additional complexity and, expense in the construction of the X-ray tube.

Hence it is desirable to provide an X-ray tube with an emitter which can effectively limit the damage caused to the emitter as a result of ion bombardment, thereby increasing the useful life of the emitter and the X-ray tube without significantly increasing the complexity or cost of the construction of the X-ray tube.

BRIEF DESCRIPTION OF THE INVENTION

There is a need or desire for an emitter that is capable of minimizing the damage done to the emitter as a result of being struck by charged gas ions formed within to increase the useful life of the X-ray tube including the emitter. The above-mentioned drawbacks and needs are addressed by the embodiments described herein in the following description.

In the present invention, a cathode is formed with one or more emitters, such as flat emitters, disposed within a cathode cup of the X-ray tube. The emitter(s) are formed with a pair of symmetric ribbon-like sections disposed adjacent one another in a central portion of the emitter and through which an emission current can be passed to generate electrons from the emitter. Due to the symmetric construction of the ribbon-like sections, any ions generated within the X-ray tube that strike the emitter will typically travel along the central axis of the emitter and strike the center of the symmetric emitter.

The ribbon-like sections on the emitter are each formed of a number of conjoined legs that extend in a parallel direction across the central section. The legs forming each section are spaced from one another to form the current path through the central portion. Further, each section in the central portion is also spaced from the other to form separate current paths through the central portion.

In one exemplary embodiment, the spaces between the legs in the sections are shortened in order to provide additional material in the ribbon/current path located at the center of the emitter. This additional material provides more area for the ions to strike without breaking the ribbon as the ion strikes occur farther away from the space between the legs, maintaining the current path intact.

In another exemplary embodiment, the legs in the central sections are shortened to form a void in the center of the emitter. The void allows the charged ions to travel through the center of the emitter without striking the material forming the emitter. In addition, certain areas of the emitter ribbon disposed around the emitter are formed of more material than in prior art emitters in order to create the void. Again, this additional material in these ribbon areas enables the emitter to withstand greater amounts of damage from ions prior to compromising the current path. In both embodiments, the additional material further reduces the damage that is done to the emitter to overheating as well as ion bombardment, as the increased amount of material causes the emitter to run at lower temperatures in those areas.

In still another exemplary embodiment, the void can additionally be formed within the emitter ribbon to have a configuration that can effectively shape the electron beam from the emitter as desired. This enables the emitter to function in the same manner as prior art emitters. Further, the emitter can be formed with a sacrificial insert or structural feature that can be positioned within the void to assist in shaping the electron beam, but which does not emit electrons therefrom. Thus, the insert can be damaged by the ionized gas without affecting the operation of the emitter.

One exemplary embodiment of the invention is an emitter assembly for an X-ray tube, including a first end, a second end and a central portion disposed between first end and the second end, the central portion including a first section extending across the central portion between the first end and the second end, the first section including first legs that define a first space therebetween and second legs that define a second space therebetween, wherein a length of the second spaces is shorter than a length of the first spaces.

Another exemplary embodiment of the invention is a method for minimizing damage to an emitter in an X-ray tube as a result of bombardment by charged ions within the X-ray tube to extend the useful life of the X-ray tube including the steps of providing an X-ray tube including a cathode assembly having a cathode cup and an emitter disposed within the cup and each configured to emit an electron beam therefrom, the emitter including a first end, a second end and a central portion disposed between first end and the second end, the central portion including a first section extending across the central portion between the first end and the second end, the first section including first legs that define a first space therebetween and second legs that define a second space therebetween, wherein a length of the second spaces is shorter than a length of the first spaces, passing a current through the emitter to generate an electron beam and allowing charged ions formed by electrons in the electron beam to strike the second legs.

Another exemplary embodiment of the invention is a cathode assembly for an X-ray tube, including a cathode cup and an emitter disposed within the cup and each configured to emit an electron beam therefrom, the emitter having a first end, a second end and a central portion disposed between first end and the second end, the central portion including a first section extending across the central portion between the first end and the second end, the first section including first legs that define a first space therebetween and second legs that define a second space therebetween, wherein a length of the second spaces is shorter than a length of the first spaces.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure

BRIEF DESCRIPTION OF THE DRAWINGS

The drawings illustrate the best mode presently contemplated of carrying out the disclosure. In the drawings.

DETAILED DESCRIPTION OF THE DRAWINGS

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Exemplary embodiments of the invention relate to an X-ray tube including an cathode assembly with a robust flat emitter. The emitter is formed of a ribbon of a material that emits electrons when heated in order to produce X-rays when the beam of electrons strikes a target. The emitter additionally includes a void disposed in the material forming the ribbon in order to form a space within the emitter through which positively charged gas ions can pass without striking and damaging the ribbon material.

Figure 1:
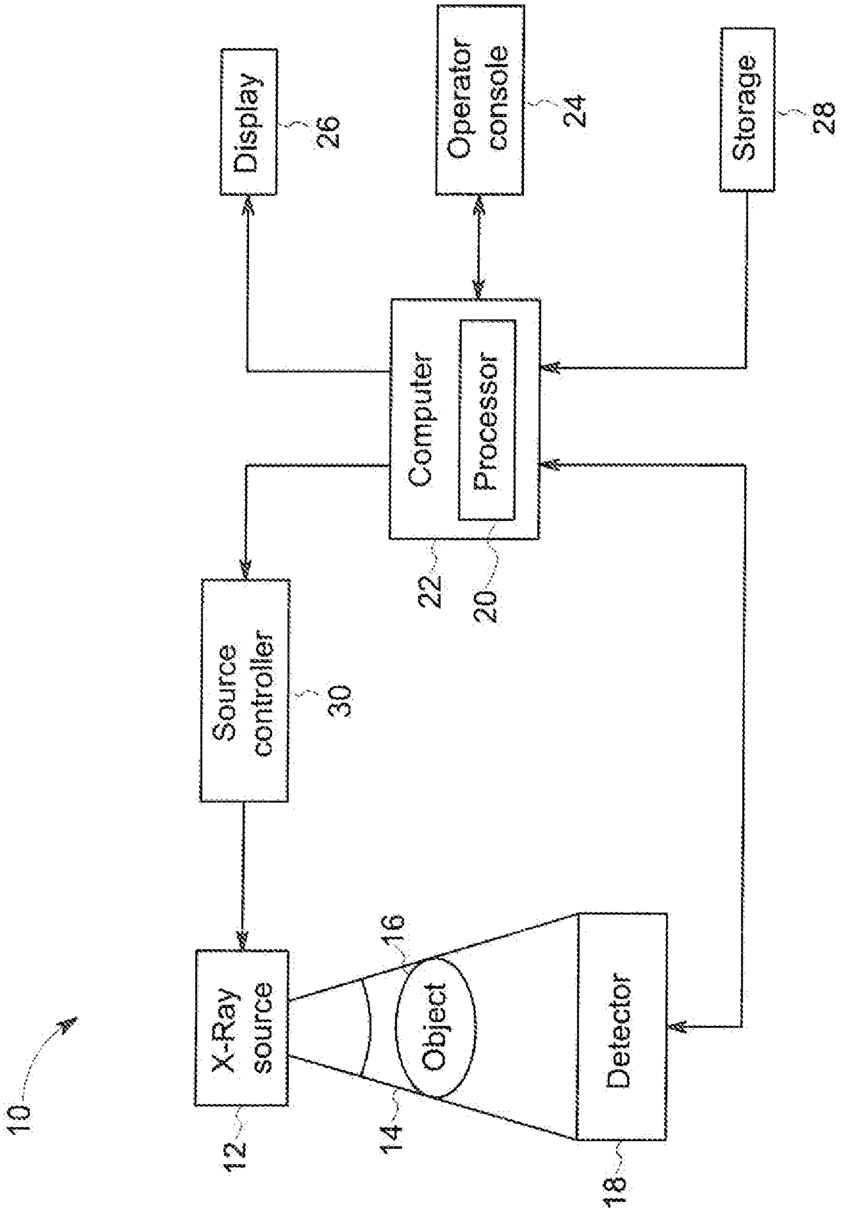
FIG. 1 is a block diagram of an imaging system according to an exemplary embodiment of the invention.

FIG. 1 is a block diagram of an embodiment of an imaging system 10 designed both to acquire original image data and to process the image data for display and/or analysis in accordance with embodiments of the invention. It will be appreciated by those skilled in the art that embodiments of the invention are applicable to numerous medical imaging systems implementing an x-ray tube, such as x-ray or mammography systems. Other imaging systems such as computed tomography (CT) systems and digital radiography (RAD) systems, which acquire image three dimensional data for a volume, also benefit from embodiments of the invention. The following discussion of x-ray system 10 is merely an example of one such implementation and is not intended to be limiting in terms of modality.

As shown in FIG. 1, x-ray system 10 includes an x-ray source 12 configured to project a beam of x-rays 14 through an object 16. Object 16 may include a human subject, pieces of baggage, or other objects desired to be scanned. X-ray source 12 may be a conventional x-ray tube producing x-rays having a spectrum of energies that range, typically, from 30 keV to 200 keV. The x-rays 14 pass through object 16 and, after being attenuated by the object, impinge upon a detector 18. Each detector in detector 18 produces an analog electrical signal that represents the intensity of an impinging x-ray beam, and hence the attenuated beam, as it passes through the object 16. In one embodiment, detector 18 is a scintillation based detector, however, it is also envisioned that direct-conversion type detectors (e.g., CZT detectors, etc.) may also be implemented.

A processor 20 receives the signals from the detector 18 and generates an image corresponding to the object 16 being scanned. A computer 22 communicates with processor 20 to enable an operator, using operator console 24, to control the scanning parameters and to view the generated image. That is, operator console 24 includes some form of operator interface, such as a keyboard, mouse, voice activated controller, or any other suitable input apparatus that allows an operator to control the x-ray system 10 and view the reconstructed image or other data from computer 22 on a display unit 26. Additionally, console 24 allows an operator to store the generated image in a storage device 28 which may include hard drives, flash memory, compact discs, etc. The operator may also use console 24 to provide commands and instructions to computer 22 for controlling a source controller 30 that provides power and timing signals to x-ray source 12.

Figure 2:
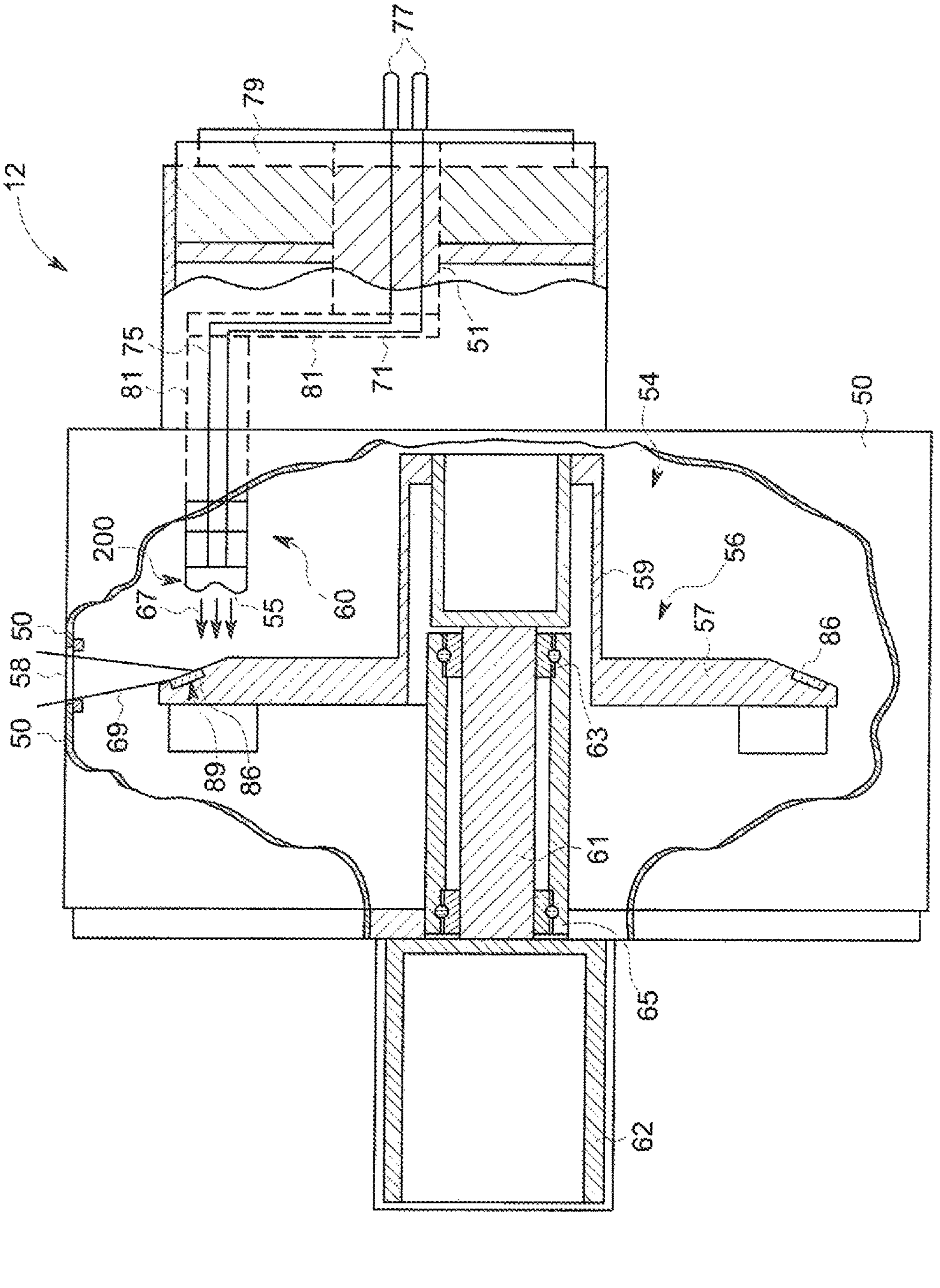
FIG. 2 is a cross-sectional view of an x-ray tube/source according to an exemplary embodiment of the invention.
Figure 3:
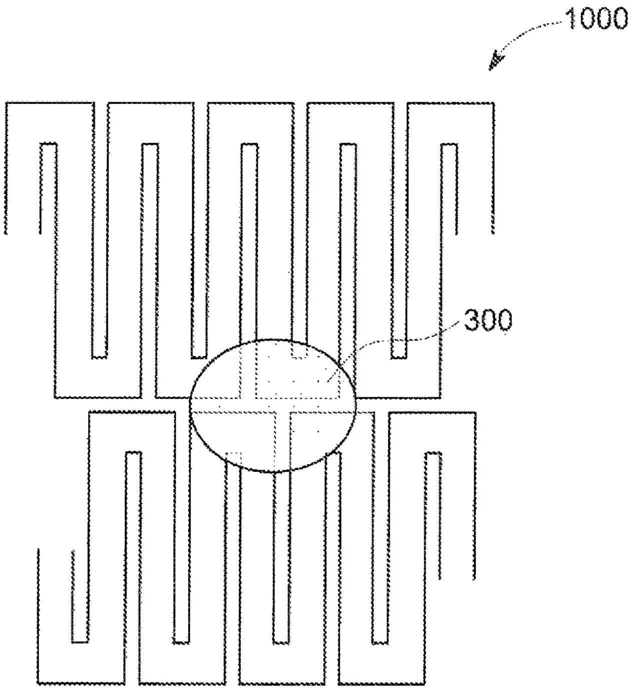
FIG. 3 PRIOR ART
FIG. 3 is a top plan view of a prior art emitter construction.

FIG. 2 illustrates a cross-sectional view of an x-ray tube 12 incorporating embodiments of the invention. X-ray tube 12 includes a frame 50 that encloses a vacuum region 54, and an anode 56 and a cathode assembly 60 are positioned therein. Anode 56 includes a target 57 having a target track 86, and a target hub 59 attached thereto. Terms "anode" and "target" are to be distinguished from one another, where target typically includes a location, such as a focal spot, wherein electrons impact a refractory metal with high energy in order to generate x-rays, and the term anode typically refers to an aspect of an electrical circuit which may cause acceleration of electrons theretoward. Target 56 is attached to a shaft 61 supported by a front bearing 63 and a rear bearing 65. Shaft 61 is attached to a rotor 62. Cathode assembly 60 includes a cathode cup 200 and a flat emitter or filament 55 formed of any suitable emissive material and coupled to a current supply lead 71 and a current return 75 that each pass through a center post 51. In operation, electrical current is carried to flat emitter 55 via the current supply lead 71 and from flat emitter 55 via the current return 75 which are electrically connected to source controller 30 and controlled by computer 22 of system 10 in FIG. 2.

Feedthroughs 77 pass through an insulator 79 and are electrically connected to electrical leads 71 and 75. X-ray tube 12 includes a window 58 typically made of a low atomic number metal, such as beryllium, to allow passage of x-rays therethrough with minimum attenuation. Cathode assembly 60 includes a support arm 81 that supports cathode cup 200, flat emitter 55, as well as other components thereof. Support arm 81 also provides a passage for leads 71 and 75. Cathode assembly 60 may have focus pads (not shown) that are either attached to cathode cup 200 or machined into cathode cup 200. Cathode assembly 60 may additionally have width and length electrodes (not shown) arranged around the emitter 55 on the cup 200 that are electrically isolated from the emitter 55. The electrodes can be operated to provide a focusing field around the emitter 55 to focus the beams of electrons 67 from the emitter 55 in a range from small to large focal spots, as well as to control the intensity of the electron beam 67 from the emitter 55.

In operation, target 56 is spun via a stator (not shown) external to rotor 62. An electric current is applied to flat emitter 55 via feedthroughs 77 to heat emitter 55 and emit electrons 67 therefrom. A high-voltage electric potential is applied between anode 56 and cathode 60, and the difference therebetween accelerates the emitted electrons 67 from cathode 60 to anode 56. Electrons 67 impinge target 57 at target track 86 and x-rays 69 emit therefrom at a focal spot 89 and pass through window 58.

Figure 4:
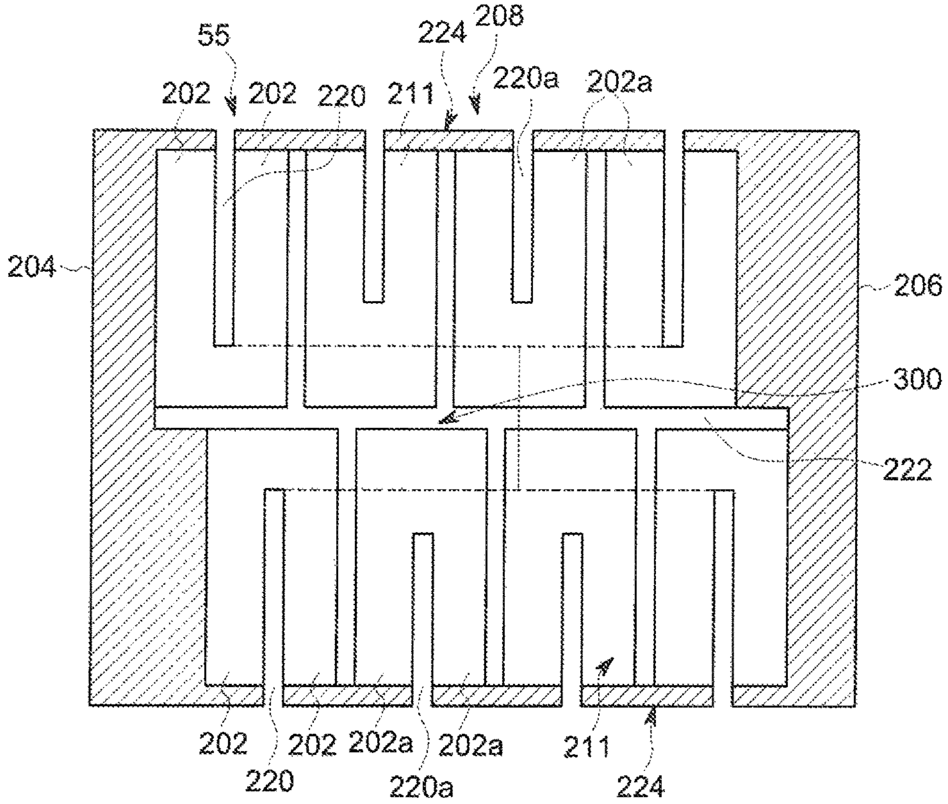
FIG. 4 is a top plan view of an emitter construction according to an exemplary embodiment of the invention.
Figure 5:
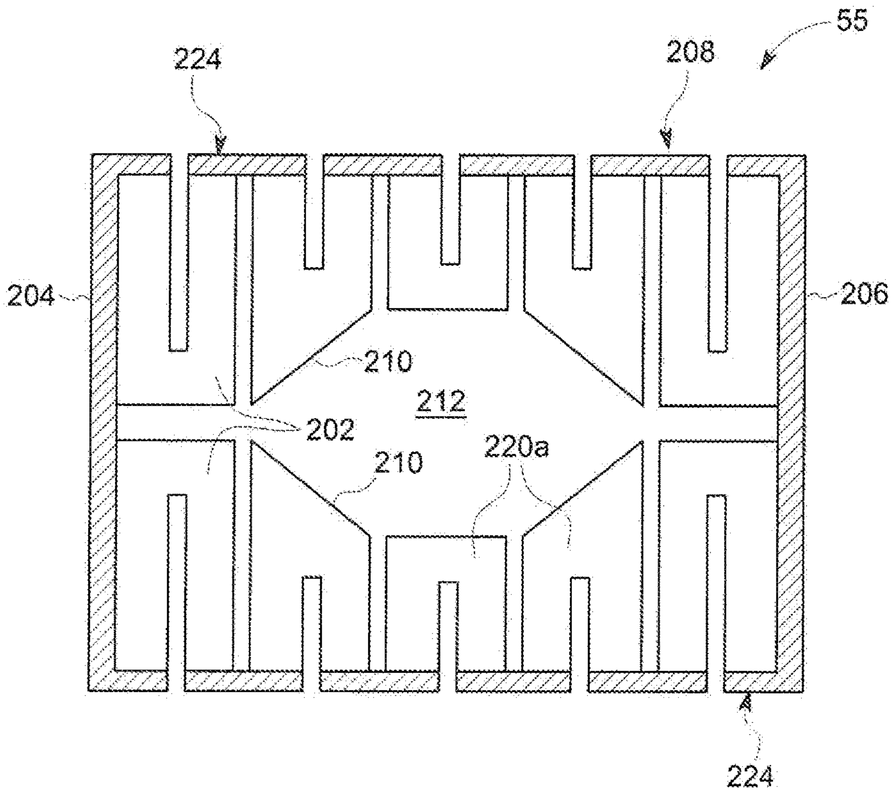
FIG. 5 is a top plan view of an emitter construction according to another exemplary embodiment of the invention.
Figure 6:
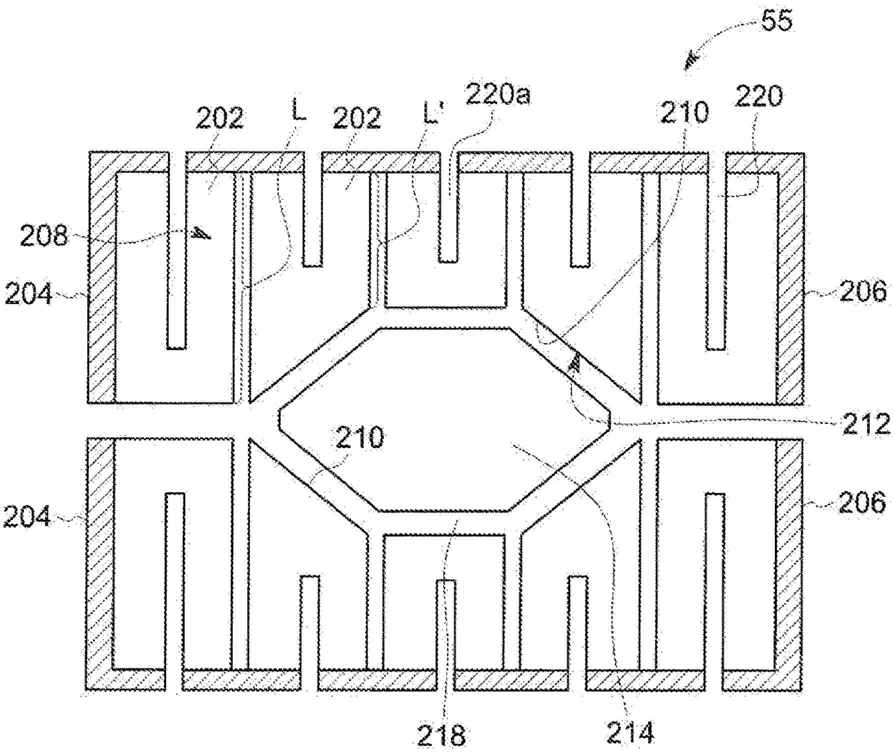
FIG. 6 is a top plan view of an emitter construction according to still another exemplary embodiment of the invention

Referring now to FIGS. 4-6, the cup 200 includes a number of emitters/emitter assembly 55 disposed on the cup 200. The emitters 55 can be formed in any suitable manner and of any suitable material, such as that disclosed in co-pending and co-owned U.S. Non-Provisional patent application Ser. No. 14/586,066, entitled Low Aberration, High Intensity Electron Beam For X-Ray Tubes, filed on Dec. 30, 2014, the entirety of which is expressly incorporated herein by reference for all purposes.

The emitter 55 is positioned on and electrically coupled to the cup 200 to be at the same potential as the cup or cathode 200 via respective attachment surfaces (not shown) on the cup 200 which are electrically insulated from each other such that no positive voltages are present around the emitter 55 as is the case in conventional cathode designs. Flat emitters 55 typically range in thickness from 100 to 500 microns but are not limited thereto. In one exemplary embodiment the thickness of the emitter 55 is 300 microns or less, however one skilled in the art will recognize that the thickness can be selected as desired depending upon the particular application. To obtain focal spot sizes relevant for medical imaging, in one exemplary embodiment of the invention, the width of the emitters 55 is typically within 2-6 mm and the length is typically within 6-15 mm. However, the sizes and/or shapes of the emitter 55 can be altered in order to provide different focusing attributes, i.e., to obtain very large and very small focal spots, to the cathode assembly 60 based on the sizes and/or shapes of the emitters 55. In addition, in the exemplary embodiments where multiple emitters 55 are present on the cup 200, the emitters 55 can be selectively operated together or separately from one another in order to achieve the desired focal spot on the target 57.

In the exemplary embodiment illustrated in FIG. 4, the emitter assembly 55 disposed on the cup 200 is thrilled with a number of interconnected legs 202 that are formed in a central portion 208 of the emitter 55 that extends between one end 204 of the emitter 55 and the opposite end 206 to define a pair of current paths 211 across the central portion 208. The legs 202 are separated by spaces 220 formed therebetween, with a separate gap 222 formed between the adjacent sections 224 of the central portion 208 that contain the separate current paths 211. While the legs 202 in each section 224 are illustrated in the exemplary embodiment as being offset form one another, it is also contemplated that the legs 202 in each section 224 can be aligned with each other. When current is passed through the emitter 55, the legs 202 are heated and emit the electrons 67 that are directed towards the target 57.

In the central portion 208 of the emitter 55, the legs **202*a* disposed immediately adjacent the center 300 of the emitter 55 are formed to be the same overall length L as legs 202, but with spaces 220*a* that are shorter than the spaces 220 in adjacent legs 202, with spaces 220*a* optionally being formed with different lengths from one another as well. This provides additional material in the current path 211 on each leg 202*a* near the center 300 of the emitter 55, such that the leg 202*a* can withstand additional ion bombardment prior to the damage causing the space 220*a* to extend completely through the associated leg 202*a* and severing the current path 211. As such, during operation of the emitter 55, when an electron 67 generated by the emitters 55 strikes a particle of residual gas (not shown) remaining within the X-ray tube 12, the electron 67 will ionize the gas creating a charged ion. This ion will be drawn towards the center 300 of the emitter 55 but will strike the leg 202***a* in the larger portion of the legs 202*a*, as opposed to legs 202, thereby extending the life of the emitter 55 and the X-ray tube 12.

Referring now to the illustrated exemplary embodiment in FIG. 5, the legs 202*a* around the center 300 of the emitter 55 are formed with shorter spaces 220*a* than spaces 220 present in adjacent legs 202, as in the embodiment of FIG. 4. However, the legs 202*a* are additionally formed to have a length L' that is shorter on at least one part of the leg 202*a* from the length L of the legs 202 disposed on either side of the central portion 208. In forming the legs 202*a* with the shorter length L', a void 210 is formed in each section 224 of the central portion 208 of the emitter 55. The void 210 can have any suitable configuration as defined by the alterations in the length dimension L' of each of the legs 202*a* disposed in the central portion 208 of the emitter 55. Also, the particular length L' can vary between legs 202*a*, as long as the length L' for any portion of a particular leg 202*a* is shorter than length L for legs 202, as shown in FIG. 5, where a first portion of the second legs 202*a* have a length L' over the entire second leg 202*a* and a second portion of the second legs 202*a* have a length dimension L' on only a part of the second leg 202*a*. Further, while the legs 202/202*a* in each section 224 are illustrated in the exemplary embodiment as being aligned with one another, it is also contemplated that the legs 202/202*a* in each section 224 can be offset from each other.

When the emitter 55 is disposed on the cup 200, the first and second voids 210 in each section 224 are disposed adjacent one another to create an aperture 212 in the center 300 of the emitter 55. In the exemplary embodiment of FIG. 5, the voids 210 are shaped as mirror images of one another, though other configurations are also contemplated as being within the scope of the invention. During operation of the emitter 55, when an electron 67 generated by the emitters 55 strikes a particle of residual gas (not shown) remaining within the X-ray tube 12, the electron 67 will ionize the gas creating a positively charged ion. This ion will be drawn towards the emitter 55 but will pass through the aperture 212 formed by the voids 210 without contacting and damaging the legs 202*a* surrounding the aperture 212. In this manner, the length of the useful life of the emitter 55 and the associated tube 12 is extended as a result of minimizing the damage to the emitter 55 from bombardment by the ions.

With regard to the configuration of the voids 210 and of the resulting aperture 212, while the aperture 212 can have any suitable shape, such as polygonal in the illustrated exemplary embodiment, the aperture 212 can additionally be configured to have any desired shape, such as a contour that assists in shaping the beam of electrons 67 produced by the emitter 55. Further, with regard to FIGS. 4 and 5, in another exemplary embodiment, the legs 202/202*a* as well as the aperture 212 can be formed in a suitable manner on completely separate emitters 55 that are subsequently positioned adjacent one another on the cup 200.

Figure 7:
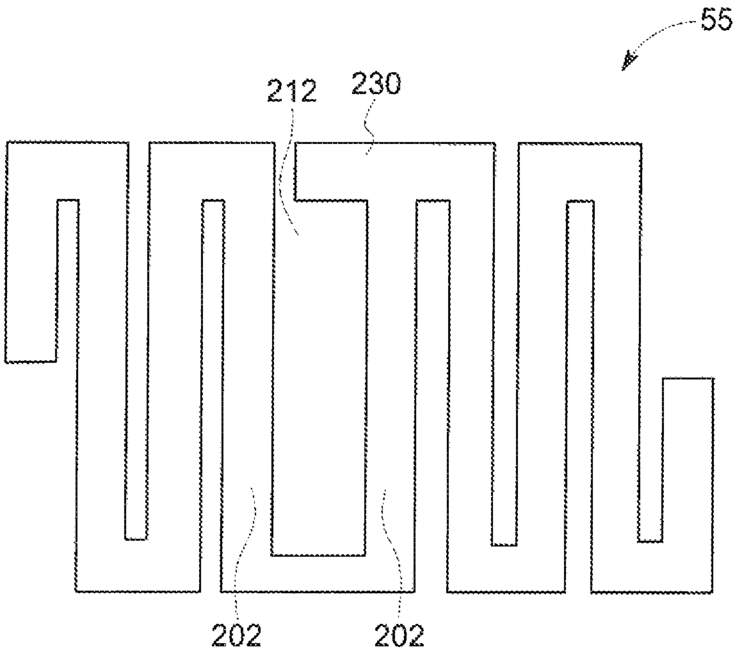
FIG. 7 is a top plan view of an emitter construction according to another exemplary embodiment of the invention.
Figure 8:
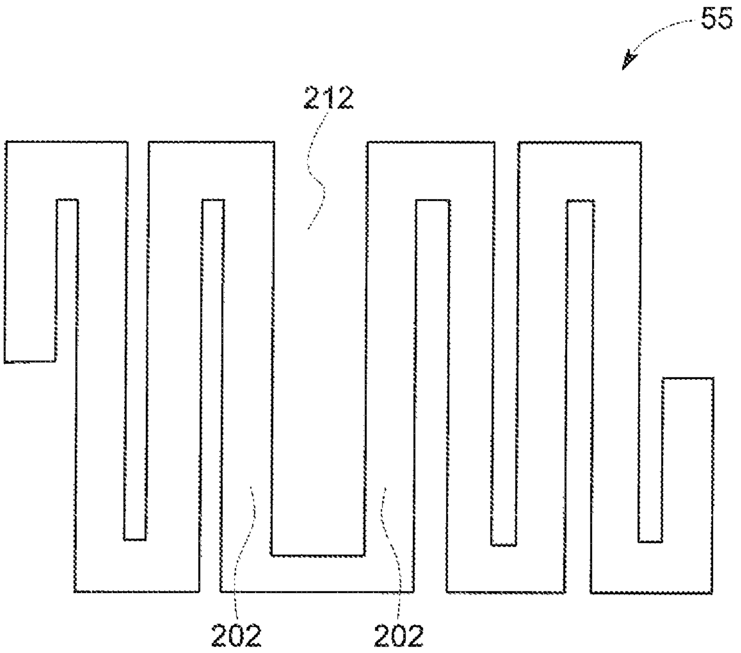
FIG. 8 is a top plan view of an emitter construction according to another exemplary embodiment of the invention.

In addition, looking now at FIGS. 7 and 8, the aperture 212 can be formed using a single emitter 55 which can form a single current path 211 across the emitter 55. In the illustrated exemplary embodiments in FIGS. 7 and 8, one of the legs 202 near the center 300 of the emitter 55 is omitted to form the aperture 212 in the emitter 55. The Aperture 212 can be unbounded on one end, as shown in FIG. 8 or one or both of the legs 202 adjacent the aperture 212 an include an extension 230 that extends from the leg 202 across the aperture 212 to a point adjacent the opposed leg 212.

Referring now to FIG. 6, in another exemplary embodiment of the invention, the aperture 212 formed between the sections 224 of the central portion 208 of the emitter 55 can have a sacrificial structure 214 positioned within the aperture 212. The structure 214 is not directly connected to the emitter 55 and defines a space 216 between the structure 214 and the emitter 55. The structure 214 can be formed of any suitable material that can withstand high temperatures in the vicinity of the emitter, such as Tungsten, Molybdenum, Niobium, or Kovar, and includes a shape complementary to that of the aperture 212, though other configurations for the structure 214 are also contemplated as being within the scope of the invention. The structure 214 provides a sacrificial portion to the emitter 55 that can be struck by the gas ions without degrading the current paths 211 formed on the emitter 55. Further, in exemplary embodiments where the structure 214 is electrically isolated from the emitter 55, the structure 214 can be charged or biased, e.g., applying a biasing voltage to the structure 214, in a known manner to assist the emitter 55 in shaping the beams of electrons produced by the emitter 55. Also, while the legs 202/202*a* in each section 224 are illustrated in the exemplary embodiment as being aligned with one another, it is also contemplated that the legs 202/202*a* in each section 224 can be offset from each other.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An emitter assembly for an X-ray tube, the emitter comprising:

a first end adapted to be operably connected to a current supply lead;

a second end adapted to be operably connected to a current return lead; and a central portion disposed between first end and the second end to provide at least one current path from the first end to the second end, the central portion including a first section extending across the central portion between the first end and the second end, the first section including first legs that define a first space therebetween and second legs that define a second space therebetween, wherein a length of the second spaces is shorter than a length of the first spaces, and wherein the first legs have a length dimension L and at least a portion of the second legs have a length dimension L', where the length L' is shorter than the length L to define a first non-linear void in the central portion.

2. The emitter assembly of claim 1, wherein the void is polygonal in shape.

3. The emitter assembly of claim 1, further comprising:

a first emitter including a first end, a second end and the first section disposed between first end and the second end, the first section including first legs having a length L and second legs having a length dimension L', where the length L' is shorter than the length L to define a first void in the first section; and a second emitter positioned adjacent the first emitter and including a first end, a second end and a second section disposed between the first end and the second end, the second section including first legs having a length dimension L and second legs having a length dimension L', where the length L' is shorter than the length L to define a second void in the second section, wherein the first void and the second void are positioned adjacent one another to form an aperture between the first emitter and the second emitter.

4. The emitter assembly of claim 3, wherein the first void and the second void are shaped as mirror images of one another.

5. The emitter assembly of claim 4, wherein the aperture is polygonal in shape.

6. The emitter assembly of claim 1, further comprising a sacrificial structure positioned within the first void.

7. The emitter assembly of claim 6, wherein the structure is shaped complementary to the first void.

8. The emitter assembly of claim 1, wherein a first portion of the second legs have a length L' over the entire second leg and a second portion of the second legs have a length dimension L' on only a part of the second leg.

9. An emitter assembly for an X-ray tube, the emitter comprising:

a first end adapted to be operably connected to a current supply lead;

a second end adapted to be operably connected to a current return lead; and a central portion disposed between first end and the second end to provide at least one current path from the first end to the second end for emission of electrons therefrom, the central portion including a first section extending across the central portion between the first end and the second end, the first section including first legs that define a first space therebetween and second legs that define a second space therebetween, wherein a length of the second spaces is shorter than a length of the first spaces, and wherein the first legs and second legs have the same length L.

10. The emitter assembly of claim 9, wherein the central portion includes the first section and a second section formed as mirror images of one another, the first section and the second section each extending across the central portion between the first end and the second end and defining a gap therebetween.

11. The emitter assembly of claim 10, wherein the first section and the second section are offset from one another.

12. The emitter assembly of claim 9, wherein the second legs are disposed immediately adjacent a center of the central section.

13. A cathode assembly for an X-ray tube, the cathode assembly comprising:

an emitter configured to emit an electron beam therefrom, the emitter including:

a first end;

a second end; and a central portion disposed between first end and the second end, the central portion including a first section extending across the central portion between the first end and the second end, the first section including first legs that define a first space therebetween and second legs that define a second space therebetween, wherein a length of the second spaces is shorter than a length of the first spaces, wherein the first legs have a length dimension L and at least a portion of the second legs have a length dimension L', where the length L' is shorter than the length L to define a first non-linear void in the central portion.

14. The cathode assembly of claim 13, further comprising a sacrificial structure positioned within the first void.

15. A method for minimizing damage to an emitter in an X-ray tube as a result of bombardment by charged ions within the X-ray tube to extend the useful life of the X-ray tube, the method comprising the steps of:

providing an X-ray tube including a cathode assembly having an emitter configured to emit an electron beam therefrom, the emitter including a first end, a second end and a central portion disposed between first end and the second end, the central portion including a first section extending across the central portion between the first end and the second end, the first section including first legs that define a first space therebetween and second legs that define a second space therebetween, wherein a length of the second spaces is shorter than a length of the first spaces, and wherein a length of the first legs is equal to a length of the second legs;

passing a current through the emitter to generate an electron beam;

allowing charged ions formed by electrons in the electron beam to strike the second legs.

16. A method for minimizing damage to an emitter in an X-ray tube as a result of bombardment by charged ions within the X-ray tube to extend the useful life of the X-ray tube, the method comprising the steps of:

providing an X-ray tube including a cathode assembly having an emitter configured to emit an electron beam therefrom, the emitter including a first end, a second end and a central portion disposed between first end and the second end, the central portion including a first section extending across the central portion between the first end and the second end, the first section including first legs that define a first space therebetween and second legs that define a second space therebetween, wherein a length of the second spaces is shorter than a length of the first spaces;

passing a current through the emitter to generate an electron beam;

allowing charged ions formed by electrons in the electron beam to strike the second legs, wherein the first legs have a length dimension L and at least a portion of the second legs have a length dimension L', where the length L' is shorter than the length L to define a first non-linear void in the central portion, and further comprising the step of allowing charged ions formed by electrons in the electron beam to pass through the first non-linear void.

17. The method of claim 16, wherein a sacrificial structure is positioned within the first void, and further comprising the step of allowing charged ions formed by electrons in the electron beam to strike the sacrificial structure.

18. The method of claim 17, further comprising the step of shaping the electron beam from the emitter using a bias voltage applied to the sacrificial structure.

* * * * *